(12) United States Patent
Ramsbottom et al.

(10) Patent No.: US 7,375,097 B2
(45) Date of Patent: *May 20, 2008

(54) INCREASING ATP AVAILABILITY BY INHIBITION OF CREATINE KINASE (CK) LEAKAGE RESULTING FROM HIGH-INTENSITY EXERCISE

(75) Inventors: James D. Ramsbottom, Mississauga (CA); Jason R. Peters, Mississauga (CA); Shan Chaudhuri, Mississauga (CA)

(73) Assignee: Aplodan Formulations Ltd., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/468,657

(22) Filed: Aug. 30, 2006

(65) Prior Publication Data

US 2008/0058289 A1    Mar. 6, 2008

(51) Int. Cl.
*A61K 31/66* (2006.01)
(52) U.S. Cl. .................................................. 514/114
(58) Field of Classification Search ............... None
See application file for complete search history.

(56) References Cited

U.S. PATENT DOCUMENTS

| 6,602,512 B1 * | 8/2003 | Cavazza ............... 424/400 |
| 2005/0192183 A1 | 9/2005 | Gastner et al. |

FOREIGN PATENT DOCUMENTS

FR    6401    11/1968

OTHER PUBLICATIONS

International Search Report, PCT/CA2006/001427, International filing date of Aug. 30, 2006, Aplodan Formulations Ltd. et al.
Van Beekvelt MC et al. Performance of near-infrared spectroscopy in measuring local O(2) consumption and blood flow in skeletal muscle. J Appl Physiol. Feb. 2001;90(2):511-9.
Verkerke GJ et al. Precision, comfort and mechanical performance of the Quadriso-tester, a quadriceps force measuring . . . Med Biol Eng Comput. May 2003;41(3):283-9. (Abstract).
Holm P et al. Endurance training of respiratory muscles improves cycling performance in fit young cyclists.BMC Physiol. May 6, 2004;4:9.
Wassermann K et al. Determination of the anaerobic threshold by gas exchange: biochemical considerations, methodology . . . Z Kardiol. 1994;83 Suppl 3:1-12. (Abstract).
Cole MA, Brown MD. Response of the human triceps surae muscle to electrical stimulation during varying levels of blood . . . Eur J Appl Physiol. May 2000;82(1-2):39-44. (Abstract).
Pincivero DM et al. Assessment of the reliability of high-intensity quadriceps femoris muscle fatigue. Med Sci Sports Exerc. Feb. 2001;33(2):334-8. (Abstract).
Nowak DA, Hermsdorfer J. [Analysis of grip force during object manipulation. Method for the objective . . . ] Nervenarzt. Aug. 2004;75(8):725-33. Review, German. (Abstract).
Hespel P et al. Creatine supplementation: exploring the role of the creatine kinase/phosphocreatine system in . . . Can J Appl Physiol. 2001;26 Suppl:S79-102. Review. (Abstract).
Boutellier U. Respiratory muscle fitness and exercise endurance in healthy humans. Med Sci Sports Exerc. Jul. 1998;30(7): 1169-72.
Marzo A, Ghirardi P. Distribuzione sucellulare del creatinolo 0-fosfato nel cuore isolto di ratto. Boll. Soc. It. Biol. Sper., 1974 50: 1601-1605. (and translation to English).
Marzo A. Ghirardi P. Pharmacokinetics of creatinol O-phosphate. Plasma turnover, fate and excretion rate, subcellular distribution . . . Arzneimittelforschung. 1979:29(9a):1452-6.
Ferrari G. Casagrande C. Synthesis and chemical properties of N- and O-phosphorylated derivatives of creatinol. Arzneimittelforschung. 1979;29(9a):1446-9.
Godfraind T. Godfrain-De Becker A. Creatinol O-phosphate is a potential intracellular buffer. Proc of the B.P.S. Sep. 1980. (Abstract).
Melloni GF et al. Acute clinical tolerance of creatinol O-phosphate. Arzneimittelforschung. 1979:29(9a):1447-9.
Nicaise J. Creatinol O-phosphate (COP) and muscular performance: a controlled clinical trial. Curr Ther Res Clin Exp. Jun. 1975;17(6):531-4.
Curti PC. Camerota G. Controllo clinco di farmaci e medicamenti. Progr. Med., Roma 30:977, 1974. (and translation to English).
Possibilità di supporto energetico nell'activitá sportivà. Stampa Medica Flash. May 1986 Anno 1 (4):1-5. (and translation to English).
De Gasperi R et al. Influenza del creatinolo o-fosfato sulla contrazione muscolare aspetti biochimici. Archivio Medicina Interna. 1981 3:351-358. (and translation to English).
Gaggino R, et al G. Aspetti metabolici delle prestatzioni sportive anaerobiche lattacide massimali. Medicina Dello Sport. 1984 37:85-92. (and translation to English).
Spengler CM, Boutellier U. Breathless Legs? Consider Training Your Respiration. News Physiol Sci. Apr. 2000;15:101-105.
Aplodan® effervescente ad alte dosi. Prescrivibile S.S.N. negli stati di insufficienza della muscolaturea striata. Simes. A (and translation to English), date unavailable.
Aplodan®. Protegge la fibra muscolare dallo stress ipossico. Aumenta la resistenza alla fatica. Simes. B. (and translation to English), date unavailable.

(Continued)

*Primary Examiner*—Raymond J Henley, III
(74) *Attorney, Agent, or Firm*—Fitzpatrick, Cella, Harper & Scinto

(57) ABSTRACT

The present invention relates to a method of increasing Adenosine Triphosphate levels in a mammal wherein 2-(carbamimidoyl-methyl-amino)ethoxyphosphonic acid inhibits the leakage of the Adenosine Triphosphate-dependant enzyme Creatine Kinase. Via the inhibition of Creatine Kinase leakage, Adenosine Triphosphate is not utilized in the conversion of creatine to phosphocreatine, thereby making it available for use in muscular contractions. The increase in availability leads to longer endurance and more forceful muscular contractions.

3 Claims, No Drawings

OTHER PUBLICATIONS

Aplodan®. Protegge la fibra muscolare dallo stress ipossico. Aumenta la resistenza alla fatica. Simes. C. (and translation to English), date unavailable.

Aplodan®. Simes. D. (and translation to English), date unavailable.

Aplodan®. Astra-Simes S.p.A. D (and translation to English), date not provided.

Croche G. Phosphatase activity of guinea-pig tissues on Creatinol O-phosphate in vitro. J. Pharm. Pharmac. 1971 24:742-743.

Ferrini R, Miragoli G. Protective effect of creatinol O-phosphate (COP) on some experimental arrhythimias in vitro and in vivo. Arzneimittelforschung. 1979;29(9a):1475-7.

Ferrini R, Miragoli G. Protective effect of creatinol O-phosphate (COP) on ventricular fibrillation and death induced by . . . Arzneimittelforschung. 1979;29(9a):1473-4.

Toxicity Profile: Creatinol O-phosphate and its sodium salt. Bibra Internatioal Ltd. Surrey UK. 2002.

Creatinolfosfate. Index Nominum International Drug Discovery. Swiss Pharmaceutical Society. Eds. Medpharm Scientific Publishers. Stuttgart. 2004. p. 323.

Muller NF, Dessing RP Eds. Aplodan, European Drug Index. European Society of Clinical Pharmacy. Deutscher Apother. Verlong. Stuttgart. 1997. p. 91.

Sweetman EC. Martindale: The Complete drug Reference 32nd Ed. London Pharmaceutical Press 2002. p. 1601.

Barlattani M et al. Creatinol O-phosphate therapy in patients with inadequate coronary circulation. Double-blind clinical trial. Arzneimittelforschung. 1979;29(9a):1483-5.

Botti G, Bonatti V. Preliminary report on electrophysiological effectiveness of creatinol O-phosphate (COP) in human subjects. Arzneimittelforschung. 1979;29(9a):1491-4.

Cadel A et al. Antiarrhythmic effectiveness of creatinol O-phosphate in man. Arzneimittelforschung. 1979;29(9a):1485-7.

Godfraind T et al. The action of creatinol O-phosphate on the inotropic effect of isoprenaline in isolated rat atria and in . . . Arzneitmittelforschung. 1979;29(9a):1465-7.

Godfraind T, Saleh MM. Action of creatinol-O-phosphate on the contractility changes evoked by hypoxia and ischemia in rat . . . Arzneimittelforschung. 1984;34(9):968-72.

Godfraind T, Sturbois X. An analysis of the reduction of creatinol O-phosphate of the myocardial lesions evoked by isoprenaline . . . Arzneimittelforschung. 1979;29(9a):1457-64.

Godfraind T. Concepts leading to the development of an anti-ischemic drug. Introductory remarks. Arzneimittelforschung. 1979;29(9a):1445.

Godfraind T et al. Ionic changes evoked by isoprenaline in rat hearts in vivo and in vitro and their reduction by creatinol . . . Arzneimit-telforschung. 1979;29(9a):1468-70.

Godfraind T. Sturbois X. The prevention of creatinol O-phosphate of myocardial lesions evoked by isoprenaline. Arch Int Pharmacodyn Ther. Feb. 1979;237(2):288-97.

Sardini D et al. Analytical aspects of Creatinol-o-phosphate. II Farmaco- Ed. Pr. 26(3):194-202, date not provided.

Knippel M et al. Effects of creatinol O-phosphate on serum enzymes in acute myocardial infarction. Arzneimittelforschung. 1979;29(9a):1480-2.

Marchetti G, Merlo L. Effects of creatinol-O-phosphate (COP) on haemodynamics and cardiac metabolism in conscious and . . . Arzneimittelforschung. 1978;28(10):1708-11.

Marchetti G et al. Effects of creatinol o-phosphate on the isolated and in situ heart. Arch Int Pharmacodyn Ther. Jun. 1971;191(2):337-44.

Marzo A, Ghirardi P. Pharmacological and toxicological properties of creatinol O-phosphate. A review. Arzneimittelforschung. 1979;29(9a):1449-52. Review.

Marzo A, Ghirardi P. Protective action of creatinol O-phosphate against serum CPK activity enhanced by isoprenaline in the rat. Arzneimittelforschung. 1979;29(9a):1471-3.

Marzo A et al. Absorption, distribution and urinary excretion of creatinol O-phosphate ( 14 C) in the guinea-pig: Arch Int Pharmacodyn Ther. Aug. 1971;192(2):378-92.

Olsen JI et al. A 31P NMR spectroscopy study of *Xenopus laevis* heart perfused in vitro with creatinol-O-phosphate, phosphocreatine . . . Pharmacol Res. Sep. 1993;28(2):135-51.

Marzo A et al. Farmacocinetica del creatinolo O-fostato. Clin Ter. Sep. 15, 1972;62(5):419-30. (and translation to English).

Cavalieri U et al. Azione del creatinolo o-fosfate sulla funzione muscolare di soggetti anziani. Clin Ter. Mar. 15, 1974;69(3):215-23. (and translation to English).

Cade R et al. Effects of phosphate loading on 2,3-diphosphoglycerate and maximal oxygen uptake. Med Sci Sports Exerc. Jun. 1984;16(3):263-8.

Kreider RB et al. Effects of phosphate loading on oxygen uptake, ventilatory anaerobic threshold, and run performance. Med Sci Sports Exerc. Apr. 1990;22(2):250-6.

Kreider RB et al. Effects of phosphate loading on metabolic and myocardial responses to maximal and endurance exercise. Int J Sport Nutr. Mar. 1992;2(1):20-47.

Nazar K et al. Phosphate supplementation prevents a decrease of triiodothyronine and increases resting metabolic rate during low . . . J Physiol Pharmacol. Jun. 1996;47(2):373-83.

Rawson NE, Friedman MI. Phosphate loading prevents the decrease in ATP and increase in food intake produced by . . . Am J Physiol. Jun. 1994;266(6 Pt 2):R1792-6.

Westerblad H et al. Muscle fatigue: lactic acid or inorganic phosphate the major cause? News Physiol Sci. Feb. 2002;17:17-21. Review.

Casey A, Greenhaff Pl. Does dietary creatine supplementation play a role in skeletal muscle metabolism and performance? Am J Clin Nutr. Aug. 2000;72(2 Suppl):607S-17S. Review.

Greenhaff PL et al. Energy metabolism in single human muscle fibres during intermittent contraction with occluded circulation. J Physiol. Jan. 1993;460:443-53.

* cited by examiner

INCREASING ATP AVAILABILITY BY INHIBITION OF CREATINE KINASE (CK) LEAKAGE RESULTING FROM HIGH-INTENSITY EXERCISE

FIELD OF THE INVENTION

The present invention relates to a method of increasing the cellular concentration of Adenosine Triphosphate, hereinafter referred to as ATP via the inhibition of the ATP-dependant enzyme Creatine Kinase, hereinafter referred to as CK.

BACKGROUND

The energy requirements of contracting muscles involved in high-intensity exercise may increase 100-fold relative to resting muscles, thereby exceeding the aerobic energy production capacity of the cells (Westerblad H, et al. News Physiol Sci. 2002 February; 17:17-21). In this case, anaerobic metabolism is required to provide additional energy. However, high-intensity exercise results in an eventual reduced capacity for muscular contractile function, or commonly known as fatigue. Thus, there is seemingly a link between anaerobic metabolism and fatigue.

In a 2000 review on the role of creatine in skeletal muscle, Casey and Greenhaff provide a thorough overview of energy supply and its utilization in muscle (Casey A, et al. Am J Clin Nutr. 2000 August; 72(2 Suppl):607S-17S). ATP is the direct energy source for contracting muscle as the energy needed for muscular contraction is released by the dephosphorylation of ATP to yield the low-energy metabolite Adenosine Diphosphate, hereinafter referred to as ADP and inorganic phosphate (Pi) according to the following reaction:

$$ATP + H_2O \rightarrow ADP + Pi + H^+ + energy \quad \text{(reaction 1)}$$

Therefore, it is naturally observed that the function of muscle is largely dependent upon the availability of ATP. However, the concentration of ATP available in muscle at rest prior to the start of exercise, is only sufficient to supply about 1-2 seconds of the energy required for intense activity. ATP, however, can be readily and rapidly regenerated through the anaerobic dephosphorylation of available phosphocreatine. However, like that of ATP, the concentration of phosphocreatine in muscle is low and only sufficient to sustain muscular activity for an additional 6 seconds. After repeated bouts of contraction, muscle phosphocreatine levels become nearly depleted (Greenhaff P L, et al. J. Physiol. 1993 January; 460:443-53). Naturally, fatigue, although likely multifaceted in terms of biochemical events, is the point at which the energy required by contracting muscle exceeds the level available either from the stored supply of ATP or the indirect synthesis of high-energy ATP through phosphocreatine dephosphorylation.

CK is an ATP-dependent enzyme, which, using magnesium, hereinafter referred to as $Mg^{2+}$, as a co-factor, phosphoylates ADP to ATP. CK is normally found within cells however, when muscle cells are damaged the cells often rupture and the normally cell-bound proteins leak out in to the surrounding serum. Since the phosphoylation reaction is ATP-dependent, an elevated presence of CK outside the cells ultimately leads to the consumption of the high-energy molecule ATP. The consumption of ATP by CK in the serum is detrimental to cells, which requires ATP as an energy source for energetic properties in relation to muscular contractions.

SUMMARY OF THE INVENTION

The foregoing needs and other needs and objectives that will become apparent for the following description are achieved in the present invention, which comprises, a method of increasing the intracellular, intercellular, extracellular and intra-tissue levels of ATP in a mammal through the inhibition of leakage of the ATP-dependant enzyme CK. In certain embodiments, the mammal is a human.

DETAILED DESCRIPTION OF THE INVENTION

In the following description, for the purposes of explanations, numerous specific details are set forth in order to provide a thorough understanding of the present invention. It will be apparent, however, to one skilled in the art that the present invention may be practiced without these specific details.

The present invention is directed towards a method of increasing the amount of ATP available in a muscle or cell via the inhibition of leakage of the ATP-dependant enzyme CK. Moreover, the present invention provides a method for the inhibition of leakage of CK from both normal cells and cells undergoing necrosis stemming from intense training or hypoxic damage wherein the result of said inhibition of CK leakage is an increase in ATP level. By way of increasing ATP levels, longer muscular endurance and more forceful muscular contractions are achieved.

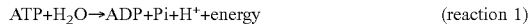

2-(carbamimidoyl-methyl-amino)ethoxyphosphonic acid

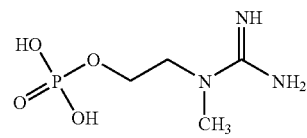

2-(carbamimidoyl-methyl-amino)ethoxyphosphonic acid is a phosphoric ester derivative of creatine. 2-(carbamimidoyl-methyl-amino)ethoxyphosphonic acid has been shown to be well tolerated and without side effects (Melloni G F et al. Arzneimittelforschung. 1979, 29(9a): 1447-9). Early studies of 2-(carbamimidoyl-methyl-amino)ethoxyphosphonic acid explored its use as a treatment for heart lesions and to restore reduced cardiac contractile function, particularly following hypoxia. (Godfraind T, et al. Arzneimittelforschung. 1984; 34(9):968-72). Furthermore, 2-(carbamimidoyl-methyl-amino)ethoxyphosphonic acid has been successfully used to improve cardiac parameters in patients with inadequate coronary blood flow (Barlattani M, et al. Arzneimittelforschung. 1979; 29(9a):1483-5).

Clinical trials have shown that 2-(carbamimidoyl-methyl-amino)ethoxyphosphonic acid has effects related to skeletal muscle performance similar to those established for creatine. 2-(carbamimidoyl-methyl-amino)ethoxyphosphonic acid has been shown to improve muscular development as well as increase the capacity to perform physical activity. In one study, hand-grip strength was improved via the administration of 2-(carbamimidoyl-methyl-amino)ethoxyphosphonic acid whereas hand-grip strength was unaffected in the placebo group (Nicaise J. Curr Ther Res Clin Exp. 1975, 17(6):531-4). Additionally, in another study conducted in elderly subjects, it was found that 2-(carbamimidoyl-methyl-amino)ethoxyphosphonic acid improved muscular performance (Cavalieri U, et al. Clin Ther. 1974, 69: 215-223).

Creatine Kinase

Creatine Kinase (CK) is an enzyme which catalyzes the following reaction:

$$ATP + creatine \leftrightarrow ADP + phosphocreatine + H^+ \quad \text{(reaction 2)}$$

Reaction 2 is reversible depending on the energy state of the cell. In fast-twitch skeletal muscles, a large pool of phosphocreatine is available for immediate regeneration of ATP hydrolyzed during short periods of intense muscle contraction. Due to high CK activity in these muscles, the CK reaction remains in a near-equilibrium state, keeping the concentration of [ADP] and [ATP] almost constant over several seconds at the expense of phosphocreatine. CK, with its involvement in ATP formation, has an impact on the onset of fatigue. Using $Mg^{2+}$ as a co-factor, CK phosphoylates ADP to ATP. Thus, since the aforementioned reaction is ATP-dependent, an elevated presence of CK in the serum ultimately leads to the consumption of the high-energy molecule ATP.

A number of parameters are associated with potential or realized damage to muscle cells and are used as diagnostic indicators, particularly for cardiac muscle cells e.g. myocardial infarction, but also for skeletal muscle cells e.g. high-intensity exercise. The measurement of CK levels in the blood is used as an assessment of muscle damage since CK is normally found within cells, specifically in the cytoplasm and in the mitochondria. When muscle cells are damaged as they are as a result of heart attacks or intense exercise, the cells often rupture and allow normally cell-bound proteins to leak out.

2-(carbamimidoyl-methyl-amino)ethoxyphosphonic acid has been shown in rats to reduce serum CK levels increased by administration of isoprenaline, a pharmacological agent known to increase cardiac activity by causing the release of calcium. As a result of this property, it is often used to induce cardiac damage in animal models of myocardial damage (Marzo A et al. Arzneimittelforschung. 1979; 29(9a): 1471-3). Further to this, 2-(carbamimidoyl-methyl-amino)ethoxyphosphonic acid has been shown to afford cardioprotection (Godfraind T, et al. Arzneimittelforschung. 1984; 34(9):968-72) and has been shown to reduce the leakage of CK as well as several other enzymes in human patients suffering from acute myocardial infarction (Knippel M, et al. Arzneimittelforschung. 1979; 29(9a):1480-2).

Therefore, at the tissue level i.e. muscle, through its protective effect, 2-(carbamimidoyl-methyl-amino)ethoxyphosphonic acid prevents the increase in CK levels occurring during muscle damage e.g. myocardial infarction or high-intensity exercise, which reflects the leakage of CK from the cytoplasm of damage cells into the blood stream. In tissue that has been subjected to damaging conditions e.g. myocardial infarction or high-intensity exercise, the number of intact and functioning cells is been reduced. This reduced cell number results in reduced CK activity at the tissue level. In turn, this reduced CK activity equates to reduced capacity to regenerate phosphocreatine, and by extension, the ability to regenerate ATP. Thus by preventing cell damage, 2-(carbamimidoyl-methyl-amino)ethoxyphosphonic acid inhibits the reduction of CK activity in muscle tissue i.e. a single, or all muscles, and thereby acts to maintain high ATP levels in highly active muscles.

Since 2-(carbamimidoyl-methyl-amino)ethoxyphosphonic acid counteracts the increase of CK, an ATP dependant enzyme in the serum, it is henceforth understood that administration of 2-(carbamimidoyl-methyl-amino)ethoxyphosphonic acid increases the amount of ATP intracellularly, intercellularly, extracellularly as well as within tissues. In resting muscle, 2-(carbamimidoyl-methyl-amino)ethoxyphosphonic acid, via its inhibition of CK leakage allows for an increase in ATP levels. In order for creatine to be transformed into phosphocreatine, ATP is required. During rest this will, therefore deplete the stock of ATP which could be used during periods where muscular contraction is required. Therefore, administration of 2-(carbamimidoyl-methyl-amino)ethoxyphosphonic acid to a mammal acts in manner to increase ATP levels within a muscle by inhibiting the leakage of the ATP dependant enzyme CK.

Oral administration in test animals has revealed that 2-(carbamimidoyl-methyl-amino)ethoxyphosphonic acid is optimally absorbed by the intestine up to about 60% at 48 hours (Marzo A, et al. Clin Ter. 1972 Sep. 15; 62(5):419-30). Moreover, 2-(carbamimidoyl-methyl-amino)ethoxyphosphonic acid was found to be stable in both alkaline and acidic solutions, an important characteristic for orally administered treatments. Additionally, in vitro testing has suggested that 2-(carbamimidoyl-methyl-amino)ethoxyphosphonic acid is dephosphorylated to creatine to some degree in the kidney, intestine and liver, and less so in the blood and muscle suggesting that intact 2-(carbamimidoyl-methyl-amino)ethoxyphosphonic acid is received by the cell in addition to supplying creatine.

Thus, the beneficial effects afforded by 2-(carbamimidoyl-methyl-amino)ethoxyphosphonic acid includes, in one aspect 2-(carbamimidoyl-methyl-amino)ethoxyphosphonic acid serving as a source of creatine through a dephosphorylated fraction; and in a second aspect protecting the cell membrane from leaking as a result of damaging conditions e.g. high-intensity exercise.

Additionally, as discussed above, it is herein understood that 2-(carbamimidoyl-methyl-amino)ethoxyphosphonic acid acts in various ways to increase the available levels of ATP within a cell. 2-(carbamimidoyl-methyl-amino)ethoxyphosphonic acid has been shown to be protective against cellular necrosis in models of myocardial infarction. As such, in protecting against necrosis, 2-(carbamimidoyl-methyl-amino)ethoxyphosphonic acid provides a method decreasing CK in the serum through the prevention of necrosis under hypoxic conditions. Such conditions are also induced during period of intense exercise. Furthermore, it is well known in the art that exercise training can induce cellular necrosis and thus a leakage of the cellular contents including CK. Moreover, CK levels are also increased following cellular damage. CK is then available in excess as substrate for ATP, thus CK uses ATP which but for the increased levels of CK would be stored for future use as an energy source, converting it to ADP which is devoid of energetic properties in relation to muscular contractions. Therefore, as an objective of this invention, it is ascertained that administration of 2-(carbamimidoyl-methyl-amino) ethoxyphosphonic acid provides a method by which an inhibition of CK leakage results, leading to an increase in ATP. The increase in ATP can then be employed to improve muscular endurance and provide more forceful muscular contractions.

In one embodiment of the invention, a portion of 2-(carbamimidoyl-methyl-amino)ethoxyphosphonic acid is fine-milled. U.S. Provisional Application No. 60/776,325 entitled "Compositions and Method for Increasing Bioavailability of Compositions for Performance Improvement", which is herein fully incorporated by reference discloses a method of improving the absorption, palatability, taste, texture and bioavailability of compounds by increasing the solubility. The increased bioavailability of a compound or ingredients is achieved via a reduction in particle size using a "fine-milling" technique. Any acceptable fine-milling technique will result in the fine-milled particles having an average particle size of between about 50 nm to about 2 nm. The reduction in size of the particle increases the surface area-to-volume ratio of each particle, thus increasing the rate of dissolution, thereby improving the rate of absorption.

As used herein, the terms "fine-milled" and/or "fine-milling" refer the process of micronization. Micronization is a mechanical process which involves the application of force to a particle, thereby resulting in a reduction in the size of said particle.

As used herein, the term "particle size" refers to the diameter of the particle. The term "average particle size" means that at least 50% of the particles in a sample will have the specified particle size. Preferably, at least 80% of the particles in a given sample will have the specified particle size, and more preferably, at least 90% of the particles in a given sample will have the specified particle size Although the preceding specification describes a how 2-(carbamimidoyl-methyl-amino)ethoxyphosphonic acid may be utilized as an method of increasing ATP via the prevention of CK leakage, it should not be construed as the only method by which 2-(carbamimidoyl-methyl-amino) ethoxyphosphonic acid may be employed to provide an energetic function related to muscular contractions. From consideration of the specification, those of skill in the art form may determine other methods wherein 2-(carbamimidoyl-methyl-amino)ethoxyphosphonic acid may be employed to enhance muscular contractions and prolong or increase muscular endurance.

What is claimed:

1. A method of reducing serum creatine kinase levels, comprising the steps of:
   selecting a composition comprising fine-milled 2-(carbamimidoyl-methyl-amino)ethoxyphosphonic acid particles admixed with a comestible carrier, at least 50% of said fine-milled 2-(carbamimidoyl-methyl-amino)ethoxyphosphonic acid particles having a particle size between 2-50 nm;
   orally administering to a human, following exercise, an effective amount of said composition to reduce cell rupture and increase cellular concentration of adenosine triphosphate.

2. The methods according to claim 1, wherein at least 80% of said fine-milled 2-(carbomimidoyl-methyl-amino) ethoxyphosphic acid particles have a particle size between 2-50 nm.

3. The methods according to claim 1, wherein at least 90% of said fine-milled 2-(carbomimidoyl-methyl-amino) ethoxyphosphic acid particles have a particle size between 2-50 nm.

* * * * *

UNITED STATES PATENT AND TRADEMARK OFFICE
CERTIFICATE OF CORRECTION

PATENT NO. : 7,375,097 B2
APPLICATION NO. : 11/468657
DATED : May 20, 2008
INVENTOR(S) : James D. Ramsbottom et al.

It is certified that error appears in the above-identified patent and that said Letters Patent is hereby corrected as shown below:

ON THE TITLE PAGE (56) REFERENCES CITED:

Other Publications (page 1), "Wassermann K et al." should read --Wasserman K et al.--; and
    Other Publications (page 2), after "Ferrini R, Miragoli G.": "arrhythimias" should read --arrhythmias--.

COLUMN 1:

Line 58, "cells" should read --cells;--;
    Line 59, "damaged" should read --damaged,--; and
    Line 60, "in to" should read --into--.

COLUMN 3:

Line 57, "is" should read --has--.

COLUMN 5:

Line 12, "refer" should read --refer to--; and
    Line 22, "size" should read --size.--.

UNITED STATES PATENT AND TRADEMARK OFFICE
CERTIFICATE OF CORRECTION

| | |
|---|---|
| PATENT NO. | : 7,375,097 B2 |
| APPLICATION NO. | : 11/468657 |
| DATED | : May 20, 2008 |
| INVENTOR(S) | : James D. Ramsbottom et al. |

It is certified that error appears in the above-identified patent and that said Letters Patent is hereby corrected as shown below:

COLUMN 6:

Line 19, "methods" should read --method--;
Line 20, "2-(carbomimidoyl-methyl-amino)" should read
--2-(carbamimidoyl-methyl-amino)--;
Line 23, "methods" should read --method--;
Line 24, "2-(carbomimidoyl-methyl-amino)" should read
--2-(carbamimidoyl-methyl-amino)--.

Signed and Sealed this

Twenty-first Day of October, 2008

JON W. DUDAS
*Director of the United States Patent and Trademark Office*